United States Patent [19]

Tunac et al.

[11] Patent Number: 4,495,286

[45] Date of Patent: Jan. 22, 1985

[54] ANTIBIOTIC COMPLEX PRODUCING BACTERIAL CULTURE

[75] Inventors: Josefino B. Tunac, Troy, Mich.; William E. Dobson, Windsor, Canada; Blanche D. Graham, Redford Township, Wayne County, Mich.

[73] Assignee: Warner-Lambert Company, Morris Plains, N.J.

[21] Appl. No.: 497,875

[22] Filed: May 25, 1983

[51] Int. Cl.³ .......................... C12N 1/20; C12R 1/465
[52] U.S. Cl. ...................................... 435/253; 435/886
[58] Field of Search ................................ 435/253, 886

[56] References Cited

U.S. PATENT DOCUMENTS 3,089,827  5/1963  Nakazawa et al. .................. 435/83

Primary Examiner—Alvin E. Tanenholtz
Attorney, Agent, or Firm—Jerry F. Janssen

[57] ABSTRACT

A biologically pure culture of the microorganism *Streptomyces pulveraceus* subspecies *fostreus* ATCC 31906 is provided. Strain 31906 is capable of producing the CL 1565 antibiotic complex in a recoverable quantity upon cultivation in an aqueous nutrient medium containing assimilable sources of nitrogen and carbon. The CL 1565 antibiotic complex includes CL 1565-A, -B and -T sodium salt compounds that in dosage form are useful antibiotics and antitumor agents.

1 Claim, No Drawings

ANTIBIOTIC COMPLEX PRODUCING BACTERIAL CULTURE

BACKGROUND OF THE INVENTION

1. Field of the Invention

The present invention relates to a microorganism, more specifically a *Streptomyces pulveraceus* subspecies *fostreus*(isolate WP-426) in biologically pure form, that is capable of producing an antibiotic complex designated as CL 1565 complex. The latter CL 1565 complex, including sodium salt compounds that in dosage form are useful antibiotics and antitumor agents, is described in copending application Ser. No. 447,544 filed Dec. 7, 1982, which description is incorporated herewith by reference.

2. Description of the Prior Art

The known microorganism species *Streptomyces pulveraceus* identified by the designation ATCC 13875 shares several characteristics in common with the CL 1565 complex producing species of the present invention. However, *Streptomyces pulveraceus* subspecies *fostreus* is unique in several characterizing features and in its ability to produce the CL 1565 complex of antibiotic compounds.

SUMMARY OF THE INVENTION

The present invention relates to a biologically pure culture of a streptomyces microorganism, *Streptomyces pulveraceus* subspecies *fostreus*, isolated and preserved for sourcing as ATCC 31906. The Streptomyces culture of the invention was found in a soil sample collected in Sao Paulo, Brazil, and isolated from the soil sample using a suitable agar plating medium. An example of such a medium is one which contains salts such as potassium phosphate (dibasic), magnesium sulfate, potassium chloride, and ferrous sulfate, and carbon substrates such as glycerol and asparagine. The soil was pretreated with calcium carbonate before it was plated on the agar medium and incubated at a favorable temperature, preferably about 24 degrees C., to allow the development of soil microorganisms.

The organism that was isolated is a new streptomycete. The organism has been sampled and samples deposited with the American Type Culture Collection, Rockville, Md. 20852, where it is being maintained in the permanent culture collection as ATCC 31906.

The organism is also being maintained as a dormant culture in lyophile tubes, cryogenic vials, and in soil tubes at the Warner-Lambert/Parke-Davis Culture Laboratory.

Culture 31906 is capable of producing the CL 1565 antibiotic complex in a recoverable quantity upon cultivation in an aqueous nutrient medium containing assimilable sources of nitrogen and carbon.

Cultures of the novel streptomycete 31906 have morphology and coloration that vary when grown on different growth media. This is illustrated by the following tabulation (Table 1) of cultural characteristics of 31906 (Isolate 426) on various media and, for comparison, of *S. pulveraceus*, when grown side by side. In this regard, the color is given for the aerial mycelium (AM); the reverse color (R), substrate mycelium; and the soluble pigment (SP). Spore type (spiral/S, flexibilis/F, and rectus/R) and percent of each spore type are also given. The color code (shown in parenthesis) follows that of COLOR HARMONY MANUAL, 4th Ed., 1958, Eckerstrom, R. and Foss, C. E. (Eds.) Container Corp. of America, Chicago, Ill.

TABLE 1

CULTURAL CHARACTERISTICS OF *STREPTOMYCES PULVERACEUS* SUBSPECIES *FOSTREUS* 31906 AND *S. PULVERACEUS* ATCC 13875

| Medium | Sporulation and Color | | ATCC 31906 | ATCC 13875 |
|---|---|---|---|---|
| Yeast extract malt extract agar | Color | AM | Beige grey (3 ih) | Lead grey (5 ih) |
| | | R | Dark brown (4 pn) | Deep brown (3 pl) |
| | | SP | Amber (3 pe) | Oak brown (4 pi) |
| (ISP Medium-2) | Spore type and Percent | S | 20 | 60 |
| | | F | 60 | 0 |
| | | R | 20 | 40 |
| Oatmeal agar | Color | AM | Beige grey (3 ih) | Silver grey (5 fe) |
| | | R | Silver grey (3 fe) | Marigold (3 la) |
| | | SP | Light beige (3 ec) | Bamboo (2 ge) |
| (ISP Medium-3) | Spore type and percent | S | 90 | 90 |
| | | F | 10 | 10 |
| | | R | 0 | 0 |
| Inorganic salts Starch agar | Color | AM | Lead grey (5 ih) | Camel (3 ge) |
| | | P | Ebony (3 po) | Dark brown (4 pn) |
| | | SP | None | Bamboo (2 gc) |
| (ISP Medium-4) | Spore type and percent | S | 90 | 80 |
| | | F | 10 | 10 |
| | | R | 0 | 10 |
| Glycerol-asparagine agar | Color | AM | Grey (3) | Grey (g) |
| | | R | Dark brown (6 pn) | Cocoa brown (5 ni) |
| | | SP | Tile red (5 ne) | Yellow maple (3 ng) |
| (ISP Medium-5) | Spore type and percent | S | 10 | 50 |
| | | F | 30 | 30 |
| | | R | 60 | 20 |
| Amidex corn starch agar (CIM 23) | Color | AM | Beige grey (3 ih) | Silver grey (3 fe) |
| | | R | Dark brown (6 pn) | Red mahogany (6½ pl) |
| | | SP | Cinnamon (3 le) | Cinnamon (3 le) |
| | Spore type and percent | S | 20 | 90 |
| | | F | 60 | 10 |
| | | R | 20 | 0 |
| Waksman starch agar (CIM 77)[2] | Color | AM | Beaver (4 li) | Silver grey (3 fe) |
| | | R | Lead grey (5 ih) | Honey gold (2 ic) |
| | | SP | None | None |

TABLE 1-continued
CULTURAL CHARACTERISTICS OF STREPTOMYCES PULVERACEUS SUBSPECIES FOSTREUS 31906 AND S. PULVERACEUS ATCC 13875

| Medium | Sporulation and Color | | ATCC 31906 | ATCC 13875 |
|---|---|---|---|---|
| | Spore | S | 90 | 90 |
| | type and | F | 10 | 5 |
| | percent | R | 0 | 5 |

[1]Hickey, R. J. and H. D. Tresner, "A Cobalt Containing Medium for Sporulation of Streptomyces Species", J. Bact., 64, 891-892, 1952.
[2]S. S. Waksman, "The Actinomycetes", Chronica Botanica Co., Waltham, Mass., p. 194, 1950.

The physiological characteristics of culture 31906 and the known S. pulveraceus ATCC 13875 are listed in Table 2.

TABLE 2
PHYSIOLOGICAL CHARACTERISTICS OF STREPTOMYCES PULVERACEUS SUBSPECIES FOSTREUS 3190 AND S. PULVERACEUS ATCC 13875

| | Culture 31906 (Isolate 426) | S. pulveraceus ATCC 13875 |
|---|---|---|
| Melanin Production on Tryptene-yeast ext. broth (ISP medium-1) | positive | negative |
| Peptone-yeast ext. itc agar (ISP medium-6) | positive | negative |
| Tyrosine agar (ISP medium-7) | slight | negative |
| Gelatin liquefaction | positive brown soluble pigment | positive no soluble pigment |
| Skim milk-coagulation | negative no soluble pigment | negative no soluble pigment |
| Nitrate Reduction | positive | positive |
| Carbon utilization: | (+) = cult. gr. | (−) = no growth |
| d-glucose | + | + |
| l-arabinose | + | − |
| cellulose | − | − |
| d-fructose | + | + |
| i-inositol | − | − |
| inulin | + | + |
| maltose | + | + |
| d-mannitol | − | − |
| melibiose | + | + |
| raffinose | + | + |
| rhamnose | + | + |
| sorbitol | − | − |
| sucrose | − | − |
| d-xylose | + | + |
| d-galactose | + | + |
| salicin | + | + |
| control- (no carbon) | − | − |

Preparation of Antibiotic CL-1565 Complex

The antibiotic CL-1565 complex of compounds, including compounds designated as CL 1565-A, -B, and -T, can be made by cultivating the CL 1565 complex producing culture ATCC 31906 of the invention under artificial conditions in production fermentors and isolating the materials thus produced, as described in the following Examples A, B, C, and D.

EXAMPLE A

Seed development and shake flask fermentation

The culture designated as ATCC 31906 in its dormant stage is transferred to a CIM-23 agar slant and incubated for 7-14 days at 24 degrees C. A portion of the microbial growth from the slant is used to inoculate an 18×150 mm seed tube containing 5 ml of ARM 1550 seed medium. The seed tube is shaken at 24 degrees C. for 3-4 days.

| CIM 23 agar slant | % |
|---|---|
| Amidex corn starch | 1.0 |
| N—Z amine, type A | 0.2 |
| Beef extract (Difco) | 0.1 |
| Yeast extract (Difco) | 0.1 |
| Cobaltous chloride.6H$_2$O | 0.002 |
| Agar | 2.0 |
| Distilled water | |
| ARM 1550 medium | |
| Bacto-Yeast extract (Difco) | 0.5 |
| Glucose, monohydrate | 0.1 |
| Soluble starch (Difco) | 2.4 |
| Bacto-Tryptone (Difco) | 0.5 |
| Bacto-Beef extract (Difco) | 0.3 |
| Calcium carbonate | 0.2 |
| Distilled water | |

A portion (1 ml) of the microbial growth from the seed tube is transferred to a 300 ml Erlenmeyer baffled shake flask containing 50 ml of SM 64 production medium. The inoculated flask is incubated at 24 degrees for 5 days with shaking using a gyratory shaker (2" throw) set at 180 RPM. The culture beer after five days of fermentation is tan in color, the mycelia are granular in appearance, and the pH of the fermentation beer is about 5.5.

| SM 64 Production Medium | |
|---|---|
| Whey (Kroger Dairy) | 35.0% by volume |
| Dextrin-Amidex 3411, (Corn Prod) | 1.5% by weight |
| Pharmamedia (Traders Protein) 431307 | 1.5% by weight |
| Distilled water | |

NOTE:
Adjust pH to 6.5 with sodium hydroxide

EXAMPLE B

Fermentation in 200-gallon fermentors

Seed Development

A cryogenic vial containing approximately 1 ml of culture suspension is used as the source of inoculum. The contents of this cryogenic vial are thawed and aseptically transferred to a two liter, baffled Erlenmeyer flask containing 600 ml of SD-05 seed medium. The inoculated flask is incubated for 46-48 hours at 24 degrees C., on a gyratory shaker, at 130 RPM speed.

| SD-05 Seed Medium | % |
|---|---|
| Amberex 1003 (Amber Labs) | 0.5 |
| Glucose monohydrate (Cerelose) | 0.1 |
| Dextrin-Amidex 3411 (Corn Prod) | 2.4 |
| N—Z Case (Humko Sheffield) | 0.5 |
| Spray dried meat soulubles | 0.3 |

| SD-05 Seed Medium | % |
|---|---|
| (Daylin Labs) | |
| Calcium carbonate | 0.2 |
| Distilled water | |

After 48 hours, the contents of the seed flask are transferred aseptically to a 30-liter, stainless steel fermentor containing 16 liters of SD-05 seed medium. The inoculated fermentor is incubated for 18–24 hours at 24 degrees C., stirred at 300 RPM, and sparged with air at 1 VVM rate. This microbial growth is used to inoculate the 200-gal production fermentor.

Production Fermentors

A 200-gal fermentor which contains 160 gal of SM-64 is sterilized by heating with steam from 40 min. at 121 degrees C. The medium is cooled to 24 degrees C. and then inoculated with about 16 liters of the microbial growth from the 30-liter seed fermentor. The inoculated medium is allowed to ferment for five to seven days at 24 degrees C., 190 RPM agitation, and sparged with 1 VVM air. Antifoam agents, Dow Corning "C" and polyglycol P-2000, are used to control foaming.

The production of CL 1565-A, CL 1565-B and CL 1565-T is monitored throughout the fermentation cycle by recording fermentation parameters such as pH and percent sedimentation or growth and by a high pressure liquid chromatographic procedure described below. An example of a fermentation profile in a 200-gal fermentor is shown in the following table.

| Fermentation Time (hr) | ph | % Sedimentation (growth) | Micrograms CL 1565-A/ml (HPLC Assay) |
|---|---|---|---|
| 0 | 6.0 | 0 | — |
| 12 | 5.8 | 3.6 | — |
| 24 | 5.1 | 13.3 | — |
| 36 | 5.15 | 14.7 | — |
| 48 | 5.35 | 19.3 | — |
| 72 | 5.45 | 22.0 | 3–6 |
| 96 | 5.95 | 24.7 | 10–20 |
| 118 | 7.65 | 43.3 | 50–65 |
| 132 | 7.80 | 39.3 | 60–65 |
| 142 | 7.90 | 40.0 | 60–70 |

This fermentor was harvested after 142 hours of fermentation with a harvest volume of 140 gal.

Isolation of CL 1565-A

EXAMPLE C

The harvested beer from the above fermentation is mixed with 34 kg of Celite 545 and filtered through a plate and frame filter press. The filtrate (473 liters) is percolated through a 30.5 cm [O.D.] column containing 120 liters of HP-20 resin (Gillies International, Inc., La Jolla, Calif.). The resin is then washed with water (605 liters), and 90:10 water:methanol (170 liters). Most of the CL 1565-A is then eluted from the resin with 80:20 water:methanol. High pressure liquid chromatographic analyses (HPLC), performed in the manner described below, of the ensuing eluates typically show the following elution profile.

| 80:20 water:methanol eluate | grams of CL 1565-A |
|---|---|
| #1 = 340 liters | <2 g |
| #2 = 340 liters | 11.5 g |
| #3 = 340 liters | 7.0 g |

Eluates #2 and #3 are separately concentrated and lyophilized to afford 90.2 g and 78.7 g, respectively, of dark brown solids. These products are combined and dissolved in 3 liters of water. The resulting solution is added to 27 liters of methanol with stirring. After standing overnight at 5 degrees C., the mixture is filtered and the precipitate is washed with 5 liters of methanol. The filtrate and wash are combined, concentrated in vacuo, and lyophilized to yield 104.5 g of a solid. A portion of this product (95 grams) in 1.5 liters of water is added slowly with mixing to 17 liters of 1-propanol. After one hour the resulting mixture is filtered and the precipitate is washed with 2 liters of 1-propanol. The filtrate and wash are combined, concentrated, and lyophilized to afford 57 g of a solid which, by HPLC analysis, typically contains about 15 g of CL 1565-A.

This product is chromatographed, in approximately 15 g lots, on 1.2 liters of 40 μm $C_{18}$-silica gel (Analytichem International, Inc., Harbor City, Calif.) contained in a 7.6 cm [O.D.] column. The eluent is 0.005M pH 4.5 ammonium acetate buffer followed by 0.005M pH 4.5 ammonium acetate containing 5% acetonitrile. The fractions collected are assayed by HPLC. The fractions containing CL 1565-A are pooled, concentrated, and lyophilized. A portion (570 mg) of the resulting product is rechromatographed using a Prep LC/System 500 apparatus fitted with a Prep-Pak ®-500/$C_{18}$ column (Waters Instruments, Inc., Milford, Mass.) and 0.1M pH 6.5 phosphate buffer containing 10% acetonitrile as the eluent. The major fractions, containing approximately 375 mg of CL 1565-A, are pooled and concentrated in vacuo. The aqueous solution is passed through a column containing 200 ml of HP-20 resin packed in water. The resin is then washed with 1400 ml of water and CL 1565-A5 remaining on the column is eluted with 350 ml of 50% methanol. The eluate is concentrated in vacuo and passed through a column containing 35 ml of Dowex-50X2 (Na+). The effluent (pH 5.5) and a water wash of the resin are combined and lyophilized to yield 180 mg of purified CL 1565-A, isolated as a sodium salt.

Analysis of this product shows typically that the product contains approximately 1.3 moles of sodium per 1.0 mole of parent CL 1565-A free acid. Because the free acids (CL 1565-A, CL 1565-B, and CL 1565-T) are labile, they preferably are isolated in the salt form such as the sodium salt form, preferably as the salts having about 1.0 to about 2.0 moles of sodium per 1.0 mole of free acid.

EXAMPLE D

Filtered beer (719 liters), prepared in the same manner as described above, are passed over 31 liers of Dowex-1×2 (chloride form) packed in a 30.5 cm [O.D.] column. The effluent and the subsequent water wash usually do not contain any detectable amounts of the CL 1565 components. The entire fractionation described herein is monitored by the HPLC method described below using 0.1M pH 6.8 phosphate buffer (Na+)-acetonitrile (88:12) as the solvent system. The Dowex-1 resin is then eluted with 1M sodium chloride-methanol (1:1) and the eluate is collected in two 10-liter and six 15-liter fractions. The CL 1565-A, CL 1565-B, CL 1565-T appear in eluates two through six. These fractions are combined and diluted with 246 liters of acetone. The resulting mixture is stored at 5 degrees C. overnight. The clear supernatant solution is removed and concentrated to 16 liters in vacuo. Lyophilization of this concentrate affords about 800 g of a solid. This product (740 g) is added to about 550 g of a similar product isolated in the same manner and the combined solids are dissolved in 20 liters of water. The resulting solution (pH 6.0) is chromatographed on 50 liters of HP-20 resin contained in a 15 cm[O.D.] column. Elution of the HP-20 column with 175 liters of water removes most of the CL 1565-T. Most of the CL 1565-A component is eluted with 100 liters of methanol-water (15:85); CL 1565-B and the remaining amount of CL 1565-A are eluted with 83 liters of methanol-water (50:50). The eluates richest in CL 1565-A are combined, concentrated, and lyophilized to afford a solid which, by HPLC analysis, contains about 110 g of CL 1565-A.

A 75-gram portion of this product is dissolved in two liters of 0.05M pH 6.8 phosphate buffer and further purified by chromatography on 52 liters (25 kg) of 200 *m $C_{18}$ reverse phase silica gel (Analytichem International, Inc., Harbor City, Calif.) packed in 0.05M pH 6.8 phosphate buffer (Na+) in a 15 cm [O.D.] column. The column is developed with 0.05M phosphate buffer containing increasing amounts (4.0–6.5%) of acetonitrile. The early fractions contain CL 1565-T. CL 1565-A is eluted in subsequent fractions. The fractions containing CL 1565-A as the only UV-absorbing component are pooled and concentrated in vacuo to 20 liters. This concentrate is stored overnight at 5 degrees C. and the inorganic salt that precipitates is filtered off. The filtrate is then charged on a 15 cm [O.D.] column containing 28 liters of HP-20 resin. The resin is washed with water (66 liters), and CL 1565-A is then eluted with 42 liters of methanol-water (50:50). The eluates that contain the majority of the CL 1565-A are combined (26 liters), concentrated, and lyophilized to yield CL 1565-A containing some inorganic impurities. The inorganic impurities can be removed by dissolving the product in methanol (at 50 to 100 mg/ml), filtering off any insoluble material, and converting the filtrate to an aqueous solution by continually adding water to the filtrate as it is being concentrated in vacuo. Final purification of CL 1565-A is effected by chromatography of the resulting aqueous concentrate on HP-20 resin.

Isolation of Additional CL 1565 Components

Careful chromatography of the concentrates obtained from CL 1565 beers on $C_{18}$-silica gel or HP-20 resin affords fractions that contain CL 1565 components other than CL 1565-A. CL 1565-B and CL 1565-T are isolated as essentially pure compounds. CL 1565 components A, B, and T can be readily distinguished by HPLC on a μ Bondapak ®$C_{18}$-silica gel column (3.9 mm I.D.×30 cm) using 0.05M –0.10M phosphate buffers containing varying proportions of acetonitrile at a flowrate of 1.5 ml/min and detection by ultraviolet absorption at 254 nm. Typical retention times of CL 1565-A, B, and T using the above HPLC conditions are given in the following table.

|  | Retention time (min) in: | |
| --- | --- | --- |
|  | Solvent A* | Solvent B** |
| CL 1565-T | 2.8 | <1.5 |
| CL 1565-A | 4.3 | <1.5 |
| CL 1565-B | >15 | 4.2 |

*0.05M pH 7.4 phosphate buffer-acetonitrile (87:13)
**0.05M pH 7.4 phosphate buffer-acetonitrile (78:22)

Crude beers can be assayed in the above manner except the solvent used in 0.1M pH 6.8 phosphate buffer-acetonitrile (88:12). In this case, at a flowrate of 2 ml/min, the retention times of CL 1565-T, CL 1565-A, and CL 1565-B are approximately 2.7, 5.0, and >12 minutes, respectively.

CL 1565-T is eluted earlier than CL 1565-A from HP-20 resin and from reverse phase silica gel. It can be isolated from the early fractions of the $C_{18}$-silica gel column described in example D, above, using HP-20 resin.

CL 1565-B is eluted more slowly than CL 1565-A from HP-20 resin and from reverse phase silica gel.

CL 1565-B is eluted with 50% methanol during the HP-20 chromatography of the crude Dowex-1 product described in Example D, above. This component can best be isolated by rechromatography on HP-20 followed by chromatography on 40 μm $C_{18}$-silica gel using essentially the same procedure described for the purification of CL 1565-A.

Properties of CL 1565-A, Sodium Salt

Ultraviolet Absorption Spectrum in MeOH: λmax 268 nm ($a_1^1$=805) with inflections at 259; and 278 nm.

Infrared Absorption Spectrum in KBr: Principal absorptions at: 3400, 1710, 1630, 1420, 1387, 1260, 1155, 1090, 1060, 975, 920, 820, and 775 reciprocal centimeters.

Optical Rotation $[\alpha]_D$+28.2 degrees (1.0% in 0.1M pH 7 phosphate buffer).

Elemental Analysis:

|  | % C | % H | % Na | % P |
| --- | --- | --- | --- | --- |
| Calcd. for $C_{19}H_{27.7}O_{10}Na_{1.3}P$: | 47.84 | 5.86 | 6.27 | 6.49 |
| Found: | 48.01 | 5.88 | 6.05 | 6.3 |

Mass Spectrum (via fast atom bombardment).
Calcd. for $[C_{19}H_{25}Na_2O_9P+H]+$=m/z 475; $[C_{19}H_{26}NaO_9P+H]+$=m/z 453; Found: m/z 475, 453.

360 MHz Proton Magnetic Resonance Spectrum in $D_2O$.

Principal signals at: (s=singlet, d=doublet, t=triplet, m=multiplet) 1.29 s (3H), 1,58 t (1H), 1.70 m (1H), 2.49–2.58 m (2H), 4.13–4.18 m (3H), 4.86 t (1H), 5.09 m (1H), 5.53 t (1H), 5.9–6.0 m (4H), 6.14 t (1H), 6.32 t (1H), 6.55 t (1H), 6.75 dd (1H), and 7.09 m (1H) parts per million downfield from sodium 2,2-dimethyl-2-silapentane-5-sulfonate (DSS).

$^{13}C$-Nuclear Magnetic Resonance Spectrum in $D_2O$. Principal signals at:

| peak number |  | peak number |  |
| --- | --- | --- | --- |
| 1 | 168.4 | 12 | 79.5 |
| 2 | 149.8 | 13 | 79.0 |
| 3 | 138.1 | 14 | 75.6 |
| 4 | 135.0 | 15 | 64.4 |
| 5 | 134.4 | 16 | 62.7 |

-continued

| peak number | peak number | | |
|---|---|---|---|
| 6 | 131.3 | 17 | 39.4 |
| 7 | 127.4 | 18 | 29.7 |
| 8 | 126.7 | 19 | 23.5 parts per million |
| 9 | 124.9 | | downfield from |
| 10 | 124.8 | | tetramethylsilane |
| 11 | 120.1 | | (TMS). |

The $^{31}$P-Nuclear Magnetic Resonance Spectrum in D$_2$O exhibits a doublet (J=10 Hz) at 0.504 ppm downfield from 85% phosphoric acid.

High Pressure Liquid Chromatography

Column: $\mu$ Bondapak®C$_{18}$ silica gel (3.9 mm I.D.×30 cm).
Solvent: 0.005M pH 7.3 sodium phosphate buffer-acetonitrile (90:10).
Flowrate: 2 ml/min.
Detection: ultraviolet absorption at 254 nm.
Retention time: 2.8 min.

Pharmacology

A. Animal Tumor Activity

CL 1565-A, sodium salt, exhibits antitumor activity in animal tumor models employed in the screening program of the Division of Cancer Treatment, National Cancer Institute. Results are listed in Table 3.

TABLE 3

Tumor Panel Models

| Tumor | Test Host | Inoculus | Sites | Drug Route and Schedule | Parameter | Criteria$^b$(T/C,%) |
|---|---|---|---|---|---|---|
| (Mouse Tumors) | | | | | | |
| Leukemia L1210 | BDF$_1$,CDF$_1$ | 10$^5$ ascites cells | IP | IP,QD,Days 1-9 | Survival | 125,150 |
| Leukemia P388 | BDF$_1$,CDF$_1$ | 10$^6$ ascites cells | IP | IP,QD,Days 1-9 | Survival | 120,175 |
| Melanoma B16 | BDF$_1$,B6C3 | 1/10 homogenate | IP | IP,QD,Days 1-9 | Survival | 125,150 |
| Lewis lung | BDF$_1$ | 10$^5$ cells (Brel) | IV | IP,QD,Days 1-9 | Survival | 140,150 |
| Colon Carcinoma 38 | BDF$_1$ | fragment (trocar) | SC | IP,QD,Days 2 and 9 | Tumor Weight | <42,<10 |
| Mammary Ca CD$_8$F$_1$ | CD$_8$F$_1$ | 5 × 10$^5$ cells (Brel) | SC | IP, once$^c$ | Tumor Weight | <42,<10 |
| (CD$_8$F$_1$ tests are conducted against first generation transplants from spontaneous tumors) | | | | | | |
| (Human Tumor Xenografts) | | | | | | |
| Mammary HX-1 | Nu/Nu (Swiss) | fragment | SRC | SC,QD,Days 1-10 | Tumor Weight | <20,<10 |
| Lung LX-1 | Nu/Nu (Swiss) | fragment | SRC | SC,QD,Days 1-10 | Tumor Weight | <20,<10 |

$^b$For survival assays, T/C X is computed as mean or median survival time of treated mice × 100/the survival time of controls. For tumor growth inhibition assays, T/CI is computed as mean change in weight of treated tumors × 100/mean change in weight of control tumors. For tumor weight assays, effectiveness is expressed as percentage of control tumor weight at the highest nonlethal dose.
$^c$Treatment given when median tumor weight attains 200-14 400 mg.

CL 1565-A, sodium salt, significantly prolongs the survival period of mice inoculated with mouse leukemia L1210 and is also curative when evaluated in this tumor mouse model, as can be seen from activity data summarized in Tables 4 and 5.

TABLE 4

Animal Tumor Screening Activity of CL 1565-A

| Animal Tumor | Activity* |
|---|---|
| Mouse Leukemia P3888 | X |
| Mouse Leukemia L1210 | XX(curative) |
| Mouse Colon 38 | X |
| Mouse Melanoma B16 | No |
| Mouse Mammary CD$_8$Fl | X$^a$ |
| Mouse Lewis Lung | No |
| Human Mammary Xenograft | −X |

TABLE 4-continued

Animal Tumor Screening Activity of CL 1565-A

| Animal Tumor | Activity* |
|---|---|
| Human Lung Xenograft | No |

$^a$Treatment started 34 days after tumor implant. This represents an advanced-stage tumor.
*Legend
−X = Borderline activity shown.
X = Activity shown. The initial endpoint is less stringent and is indicative of statistical significance.
XX = Outstanding activity shown and a proportion of "cures" produced. The stringent endpoint is indicative of sufficient antitumor selectivity to warrant consideration for development toward clinical trial.
No = No activity shown.

TABLE 5

Response of L1210 Leukemia to CL 1565-A

| Test Number | Dosage$^a$ mg/kg/ dose | Schedule | T/C (%)$^b$ | "Cures"$^c$ | Net Tumor Reduction$^d$ |
|---|---|---|---|---|---|
| 1 | 6.25 | Daily X 9 | 207 | 0/6$^e$ | +1.56 |
| 2 | 12.50 | Daily X 9 | 337 | 3/6$^e$ | +6.04 |
|  | 6.25 | Daily X 9 | 194 | 1/6 | +0.42 |
|  | 3.12 | Daily X 9 | 191 | 0/6 | +0.10 |
| 3 | 12.50 | Daily X 9 | 246 | 0/6$^f$ | +2.26 |
|  | 6.25 | Daily X 9 | 216 | 0/6 | +0.42 |
|  | 3.12 | Daily X 9 | 195 | 0/6 | −0.84 |
|  | 1.56 | Daily X 9 | 150 | 0/6 | −2.63 |
| 4 | 12.50 | Daily X 9 | 268 | 0/6$^g$ | +4.57 |
|  | 6.25 | Daily X 9 | 236 | 1/6 | +2.01 |
|  | 3.12 | Daily X 9 | 194 | 0/6 | −1.34 |

$^a$LD$_o$
$^b$T/C (%) = mean or median survival time of treated mice × 100/mean or median survival time of controls.
$^c$Survivors at the completion of the observation period.
$^d$Net Tumor Reduction = estimates of the reduction of viable tumor cells below that tumor burden present just prior to treatment. If the Log$_{10}$ cell kill value is positive, there were fewer cells present at the end of therapy than at the start. If negative, the tumor grew under treatment.
$^e$30-Day survivors are considered cures.
$^f$45-Day observation period.

B. Activity in Cell Culture

The ED$_{50}$ (50% inhibitory concentration in tissue culture) was determined for various tumor lines. The data are presented below:

| Tissue Culture Cells | ED$_{50}$ ($\mu$g/ml) |
|---|---|
| Lewis lung carcinoma | 1.3 |
| L1210 leukemia | 0.15 |
| HCT-8 human colon carcinoma | 1.6 |
| MCA-38 mouse colon carcinoma | 1.1 |

Properties of CL 1565-T, Sodium Salt

Ultraviolet Absorption Spectrum in MeOH: Nearly identical to that for CL 1565-A, sodium salt, with $a_1 = 774$ at *max 268 nm and inflections at 260 and 278 nm.

Infrared Absorption Spectrum in KB4: Principal absorptions at: 3400, 1715, 1630, 1380, 1260, 1090, 970, 830 and 770 reciprocal centimeters.

Mass Spectrum (via fast atom bombardment): Calcd. for $[C_{19}H_{25}Na_2O_{10}P+H]+ = m/z$ 491; Found: m/z 491.

360 MHz Proton Magnetic Resonance Spectrum in $D_2O$: The $^1H$-NMR spectrum of CL 1565-T is very similar to the $^1H$-NMR spectrum of CL 1565-A with the exception that the former spectrum exhibits a characteristic one proton signal appearing as a doublet of doublets at 4.34 ppm and is devoid of any signals between 2.2–3.2 ppm downfield from DSS.

Principal Signals of CL 1565-T, sodium salt are at: (s=singlet, d=doublet, t=triplet, m-multiplet): 1.300 s (3H), 1.55–1.64 m (1H), 1.73 t (1H), 4.13–3.20 m (1H), 4.16 d (2H), 4.34 dd (1H), 4.94 t (1H), 5.09 dd (1H), 5.55 t (1H), 5.89–6.06 m (3H), 6.16 m (2H), 6.36 t (1H), 6.56 t (1H), 6.76 dd (1H), 7.14 dd (1H) parts per million downfield from DSS.

90.4 MHz $^{13}C$-Nuclear Magnetic Resonance Spectrum in $D_2O$:

| Peak # | Chemical Shift* | Peak # | Chemical Shift* |
|---|---|---|---|
| 1 | 24.10 | 11 | 126.91 |
| 2 | 41.60 | 12 | 127.18 |
| 3 | 64.68 | 13 | 128.99 |
| 4 | 64.90 | 14 | 133.36 |
| 5 | 66.67 | 15 | 136.87 |
| 6 | 78.28 | 16 | 137.23 |
| 7 | 79.81 | 17 | 142.27 |
| 8 | 84.33 | 18 | 149.46 |
| 9 | 124.40 | 19 | 169.66 |

-continued

| Peak # | Chemical Shift* | Peak # | Chemical Shift* |
|---|---|---|---|
| 10 | 126.21 | | |

*parts per million downfield from TMS

Properties of CL 1565-B, Sodium Salt

Ultraviolet Absorption Spectrum in MeOH: *max 267 nm ($a_1 = 805$) with inflections at 259 and 277 nm.

Infrared Absorption Spectrum in KBr: Principal absorptions at: 1720, 1640, 1385, 1200, 1060, 970, and 820 reciprocal centimeters.

360 MHz Proton Magnetic Resonance Spectrum in $D_2O$: Principal Signals at: (s=singlet, d=doublet, t=triplet, m-multiplet); 1.32 s (3H), 1.58 t (1H), 1.72 t (1H), 1.79 d.

(3H), 2.45–2.68 m (2H), 4.15 t (1H), 4.89 t (1H), 5.10 m (1H), 5.49 t (1H), 5.83–6.21 m (6H), 6.50 –6.64 m (2H), 7.06–7.13 m (1H) parts per million downfield from DSS. 90.4 MHz $^{13}C$-Nuclear Magnetic Resonance Spectrum in $D_2O$:

| Peak # | Chemical Shift* | Peak # | Chemical Shift* |
|---|---|---|---|
| 1 | 20.70 | 11 | 127.24 |
| 2 | 25.06 | 12 | 129.47 |
| 3 | 31.91 | 13 | 129.90 |
| 4 | 41.85 | 14 | 134.66 |
| 5 | 66.85 | 15 | 135.94 |
| 6 | 77.87 | 16 | 139.67 |
| 7 | 80.87 | 17 | 140.42 |
| 8 | 81.64 | 18 | 152.01 |
| 9 | 122.41 | 19 | 170.56 |
| 10 | 124.45 | | |

*parts per million downfield from TMS

Having thus described our invention, what we claim and desire by Letters Patent to secure are the following:

1. A biologically pure culture of the microorganism *Streptomyces pulveraceus* subspecies *fostreus* ATCC 31906, said culture being capable of producing the CL 1565 antibiotic complex in a recoverable quantity upon cultivation in an aqueous nutrient medium containing assimilable sources of nitrogen and carbon.

* * * * *